US011079382B2

(12) United States Patent
Sebastiao et al.

(10) Patent No.: US 11,079,382 B2
(45) Date of Patent: Aug. 3, 2021

(54) METHODS, KITS, AND SYSTEMS FOR SCORING THE IMMUNE RESPONSE TO CANCER

(71) Applicant: Ventana Medical Systems, Inc., Tucson, AZ (US)

(72) Inventors: Noemi Sebastiao, Tucson, AZ (US); William Day, Tucson, AZ (US); Robert Ochs, Oro Valley, AZ (US); Srinivas Chukka, San Jose, CA (US); Jim Martin, Mountain View, CA (US); Michael Barnes, San Francisco, CA (US); Joerg Bredno, San Francisco, CA (US); Ting Chen, Sunnyvale, CA (US); Alisa Tubbs, Phoenix, AZ (US); Yao Nie, Sunnyvale, CA (US)

(73) Assignee: Ventana Medical Systems, Inc, Tucson, AZ (US)

( * ) Notice: Subject to any disclaimer, the term of this patent is extended or adjusted under 35 U.S.C. 154(b) by 182 days.

(21) Appl. No.: 15/246,409

(22) Filed: Aug. 24, 2016

(65) Prior Publication Data

US 2016/0363593 A1 Dec. 15, 2016

Related U.S. Application Data

(63) Continuation of application No. PCT/EP2015/053643, filed on Feb. 20, 2015.

(60) Provisional application No. 61/943,939, filed on Feb. 24, 2014.

(51) Int. Cl.
| | |
|---|---|
| *G01N 33/574* | (2006.01) |
| *G01N 15/14* | (2006.01) |
| *G06F 19/20* | (2011.01) |
| *G16B 25/00* | (2019.01) |
| *G01N 33/68* | (2006.01) |
| *G01N 33/566* | (2006.01) |
| *G16B 25/10* | (2019.01) |
| *G01N 35/00* | (2006.01) |
| *G01N 15/00* | (2006.01) |
| *G01N 15/10* | (2006.01) |

(52) U.S. Cl.
CPC ..... *G01N 33/5743* (2013.01); *G01N 15/1463* (2013.01); *G01N 33/566* (2013.01); *G01N 33/574* (2013.01); *G01N 33/57415* (2013.01); *G01N 33/6875* (2013.01); *G01N 35/00029* (2013.01); *G16B 25/00* (2019.02); *G16B 25/10* (2019.02); *G01N 2015/008* (2013.01); *G01N 2015/1006* (2013.01); *G01N 2015/1486* (2013.01); *G01N 2035/00138* (2013.01); *G01N 2333/4703* (2013.01); *G01N 2333/4739* (2013.01); *G01N 2333/4742* (2013.01); *G01N 2333/7051* (2013.01); *G01N 2333/70503* (2013.01); *G01N 2333/70517* (2013.01)

(58) Field of Classification Search
None
See application file for complete search history.

(56) References Cited

U.S. PATENT DOCUMENTS

| | | | |
|---|---|---|---|
| 2009/0203015 A1* | 8/2009 | Chang | C12Q 1/6886 435/6.14 |
| 2012/0329878 A1 | 12/2012 | Coussens et al. | |
| 2013/0330325 A1 | 12/2013 | Grabe et al. | |
| 2016/0081594 A1 | 3/2016 | Gaddipati et al. | |

FOREIGN PATENT DOCUMENTS

| | | |
|---|---|---|
| JP | 2012150253 A | 8/2012 |
| JP | 2013092540 A | 5/2013 |
| WO | 02086498 A1 | 10/2002 |
| WO | 2007045996 A1 | 4/2007 |
| WO | 2013107900 A1 | 7/2013 |
| WO | 2013148448 A1 | 10/2013 |
| WO | 2013186374 A1 | 12/2013 |
| WO | 2014005909 A1 | 1/2014 |

OTHER PUBLICATIONS

Stack et al. Methods 70 (2014) 46-58.*
Ellington et al. Clinical Chemistry 56:2, 186-193 (2010).*
Cimino-Mathews, A., "Metastatic triple-negative breast cancers at first relapse have fewer tumor-infiltrating lymphocytes than their matched primary breast tumors: a pilot study", Human Pathology, 2013, 2055-2063, 44.
Gannon, P.O., Characterization of the intra-prostatic immune cell infiltration in androgen-deprived prostate cancer patients, J. Immunol., 2009, 9-17, 348.
IPEA, International Preliminary Report on Patentability, International Preliminary Report on Patentability, dated Sep. 16, 2016, 1-7, N/A.
ISA, International Search Report, International Search Report, dated Jun. 3, 2015, 1-5, N/A.
ISA, ISA Written Opinion, Written Opinion, dated Jun. 3, 2015, 1-6, N/A.
Russell, S.M., "Immune cell infiltration patterns and survival in head and neck squamous cell carcinoma", Head & Neck Oncology, 2013, 1-10, 5.
Alyassin M. et al., Rapid automated cell quantification on HIV microfluidic devices, Royal Society of Chemistry, (2009), pp. 1-12, vol. 9 Issue 23.

(Continued)

*Primary Examiner* — Michael L Borin
(74) *Attorney, Agent, or Firm* — Ventana Medical Systems, Inc.

(57) ABSTRACT

This disclosure describes methods, kits, and systems for scoring the immune response to cancer through examination of tissue infiltrating lymphocytes (TILs). Methods of scoring the immune response in cancer using tissue infiltrating lymphocytes include detecting CD3, CD8, CD20, and FoxP3 within the sample and scoring the detection manually or scoring the digital images of the staining with the aid of image analysis and algorithms.

17 Claims, 9 Drawing Sheets
(9 of 9 Drawing Sheet(s) Filed in Color)

(56) References Cited

OTHER PUBLICATIONS

Cualing H. et al., "Virtual flow cytometry" of immunostained lymphocytes on microscopic tissue slides: iHCFlow™ tissue cytometry, Clinical Cytometry, (2007), pp. 63-76, vol. 4 Issue 11.
Galon et al., Type, Density, and Location of Immune Cells Within Human Colorectal Tumors Predict Clinical Outcome, Science, 2006, pp. 1960-1965, vol. 313.
Haas M. et al., Stromal regulatory T-cells are associated with a favourable prognosis in gastric cancer of the cardia, BMC Gastroenterology, (2009), pp. 1-10, vol. 9 Issue 65.
Halama N. et al., Estimation of Immune Cell Densities in Immune Cell Conglomerates: An Approach for High-Throughput Quantification, PLOS One, (2009), pp. 1-6, vol. 4 Issue 11.
Hawes, D. et al., Immunohistochemistry, Modem Surgical Pathology, (2009), pp. 48-70, Ed. 2 Chapter 5.
Krueger, J et al., Combat or surveillance? Evaluation of the heterogeneous inflammatory breast cancer microenvironment, J Pathol, (2013), pp. 569-578, vol. 229 Issue 4.
Leng, S. et al., Elisa and Multiplex Technologies for Cytokine Measurement in Inflammation and Aging Research, The Journals of Gerontology, (2009), pp. 879-884, vol. 63 Issue 8.
Nattkemper, T. et al., A neural classifier enabling high-throughput topological analysis of lymphocytes in tissue sections, IEEE Transactions on Information Technology in Biomedicine, (2001), pp. 138-149, vol. 5 issue 2.
Stumpf M. et al, Intraepithelial CD8-positive T lymphocytes predict survival for patients with serous stage III ovarian carcinomas: relevance of clonal selection of T lymphocytes, British Journal of Cancer, (2009), pp. 1513-1521, vol. 101.
Van Der Loos C., Multiple Immunoenzyme Staining: Methods and Visualizations for the Observation With Spectral Imaging, Journal of Histochemistry & Cytochemistry, (2008), pp. 313-328, vol. 56 Issue 4.
Zingg U. et al., Tumour-infiltrating lymphocytes and survival in patients with adenocarcinoma of the oesophagus, European Journal of Surgical Oncology, (2010), pp. 670-677, vol. 36 Issue 7.
Loi C et al., "Prognostic and Predictive Value of Tumor-Infiltrating Lymphocytes in a Phase III Randomized Adjuvant Breast Cancer Trial in Node-Positive Breast Cancer Comparing the Addition of Docetaxel to Doxorubicin With Doxorubicin-Based Chemotherapy: BIG 02-98," Journal of Clinical Oncology 31(7), pp. 860-867, 2013.
Capone M., et al., "Immunoscore: a new possible approach for melanoma classification", Journal for ImmunoTherapy of Cancer, 2014, 2(Suppl 3), P193 (2 pages). http://www.immunotherapyofcancer.org/content/2/S3/P193.
Bindea, G. et al., Spatiotemporal Dynamics of Intratumoral Immune Cells Reveal the Immune Landscape in Human Cancer, Supplemental Information, (2013), 39 pages, vol. 39.
"Tissue microarray", Wikipedia, https://en.wikipedia.org/wiki/Tissue_microarray, printed Nov. 26, 2019, pp. 1-3.
Stat trek: Teach yourself statistics. Combinations and Permutations Calculator, https://stattrek.com/online-calculator/combinations-permutations.aspx, downloaded Mar. 12, 2021, 3 pages.
Minutes of Oral Proceedings dated Mar. 12, 2021 in Opposition to EP Patent No. 3111221, 58 pages.
Notice of Opposition dated Jul. 16, 2019 in Opposition to EP Patent No. 3111221, 62 pages.
Reply of Patent Proprietor dated Dec. 4, 2019 in Opposition to EP Patent No. 3111221, 77 pages.
Response to Summons to Attend Oral Proceedings dated Nov. 18, 2020 in Opposition to EP Patent No. 3111221, 58 pages.
Submission from Opponent dated Jan. 10, 2020 in Opposition to EP Patent No. 3111221, 9 pages.
Summons to Attend Oral Proceedings dated Mar. 18, 2020 in Opposition to EP Patent No. 3111221, 20 pages.
Interlocutory Decision dated Mar. 15, 2021 in Opposition to EP Patent No. 3111221, 69 pages.
Pirici et al., "Antibody Elution Method for Multiple Immunohistochemistry on Primary Antibodies Raised in the Same Species and of the Same Subtype", p. 567-75, 2009, Journal of Histochemistry and Cytochemistry.†
Bindea et al., "Spatiotemporal Dynamics of Intratumoral Immune Cells Reveal the Immune Landscape in Human Cancer", p. 782-95, 2013, Immunity.†
Sasada et al., "Variation of tumor-infiltrating lymphocytes in human cancers: Controversy on clinical significance", p. 1235-51, 2011, Immunotherapy.†
Chris M. van der Loos, "Multiple Immunoenzyme Staining: Methods and Visualizations for the Observation with Spectral Imaging", p. 313-28, 2008, Journal of Histochemistry and Cytochemistry.†

\* cited by examiner
† cited by third party

FIG. 8(A)
FIG. 8(B)
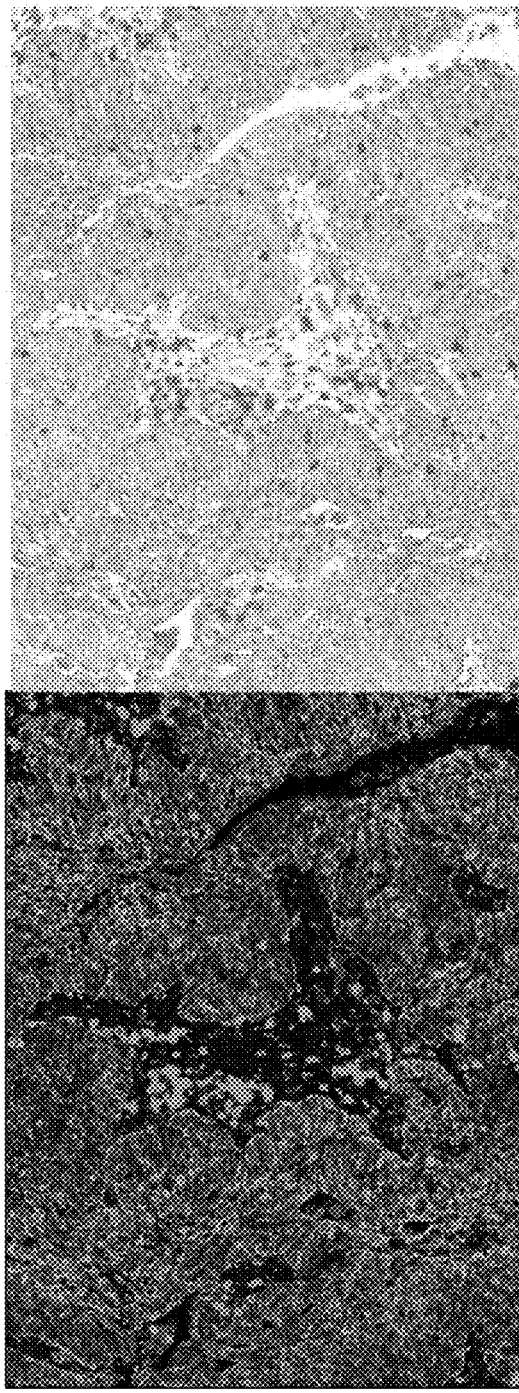
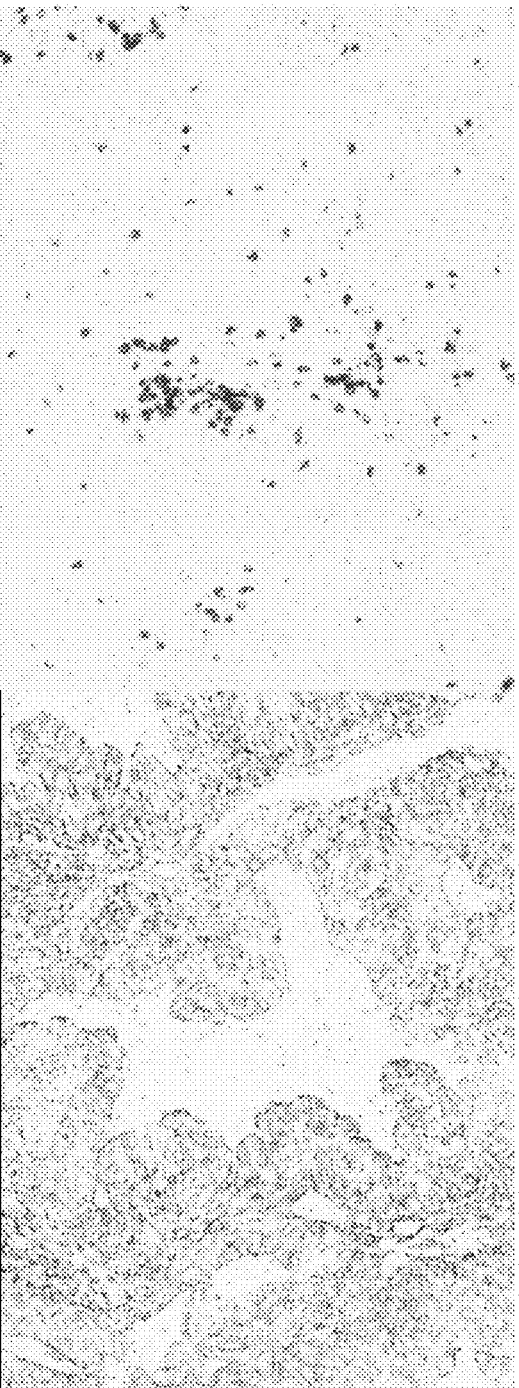
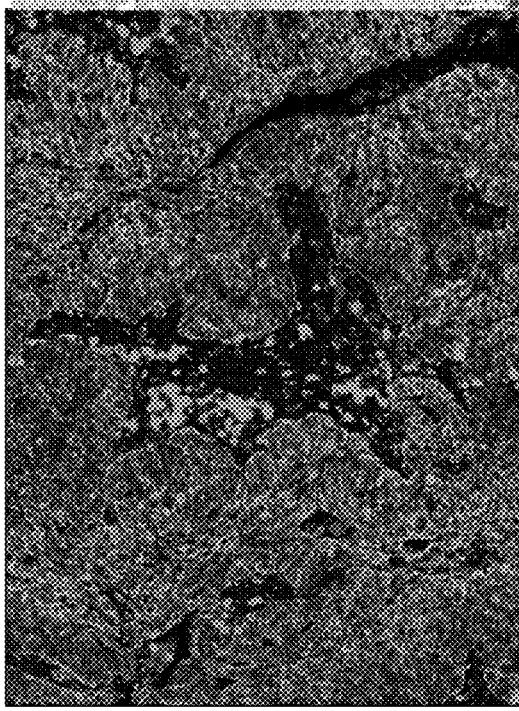
FIG. 8(C)
FIG. 8(D)

METHODS, KITS, AND SYSTEMS FOR SCORING THE IMMUNE RESPONSE TO CANCER

CROSS-REFERENCE TO RELATED APPLICATIONS

This patent application is a continuation of International Patent Application No. PCT/EP2015/053643 filed Feb. 20, 2015, which claims priority to and the benefit of U.S. Provisional Patent Application Ser. No. 61/943,939 filed Feb. 24, 2014. Each patent application is incorporated herein by reference as if set forth in its entirety.

FIELD

This disclosure relates to methods, kits, and systems for scoring the immune response to cancer through examination of tissue infiltrating lymphocytes (TILs).

BACKGROUND

Biological samples, such as histology specimens, may be examined histopathologically by light microscopy using bright field illumination; whereas molecular pathology is the examination, at a molecular level, of biomolecules associated with disease. From a histopathological examination, important information about patient diagnosis, prognosis, and treatment options can be elucidated. Pathologists study the histopathologic architecture, tissue morphology, and/or signals associated with the detection of particular biomolecules (e.g. nucleic acid or proteins). A number of assays presently available detect and/or quantify proteins (i.e. immunohistochemistry (IHC)), nucleic acids (i.e. in situ hybridization (ISH)), carbohydrates (i.e. histochemistry (HC)), and enzymes (i.e. enzyme histochemistry (EHC)).

Although the presence of immune infiltrates of variable content in human solid tumors from different origins and different patients has long been established, the prognostic value of these components is still not fully understood. There has been a shift from the turn of the $21^{st}$ century to now wherein immunity and inflammation are considered hallmarks of cancers. That is, considering published data, it is known that local inflammation strongly influences cancer development. In one example, the creation of an acute local inflammation has been used in the adjuvant treatment of superficial bladder cancer by BCG. This approach is now the state of the art for this malignancy. In contrast, chronic inflammation is understood to influence the outcome and progression of many tumors (head and neck, gastric, colorectal, etc.). Similarly, immune deficiencies have been seen as negative prognostic indicators.

However, in light of the prior art, an image analysis system for the automatic computation of an immune score from a set images of multiplex IHC slides or images of fluorescent stained slides is desirable.

SUMMARY

Methods, kits, and systems for scoring cancer through examination of tissue infiltrating lymphocytes (TILs) are disclosed in which a panel of CD3, CD8, CD20, and FoxP3 was found to be useful as a prognostic marker across a number of cancers, including high risk melanoma, colorectal cancer, and breast cancer.

Immune cells infiltrating the tumor microenvironment (TILs) may either limit or promote tumor progression. Increasing evidence demonstrate that the number, type and location of TILs in primary tumors may have a prognostic role. These observations have led to the development of potential new scoring systems derived from the immune context in tissue and based on the identification and evaluation of specific lymphocyte populations. The potential prognostic value of CD3, CD8, CD20, and FOXP3 was explored as an 'Immunoscore' for melanoma patients which would utilize widely accessible, standardized technology.

The role of the adaptive immune response in controlling the growth and recurrence of human tumors has been studied extensively. The characterization of tumor-infiltrating immune cells in cancers by gene expression profiling and in situ immunohistochemical staining has been presented. However, collectively, the immunological data (the type, density, and location of immune cells within the tumor samples) were found to be a better predictor of patient survival than the histopathological methods currently used to stage, for example, colorectal cancer. The results were validated in two additional patient populations. These data support the hypothesis that the adaptive immune response influences the behavior of human tumors. In situ analysis of tumor-infiltrating immune cells may therefore be a valuable prognostic tool in the treatment of colorectal cancer and possibly other malignancies.

The natural history of a tumor includes phases of 'in situ' growth, invasion, extravasation and metastasis. During these phases, tumor cells interact with their microenvironment and are influenced by signals coming from stromal, endothelial, inflammatory and immune cells. Indeed, tumors are often infiltrated by various numbers of lymphocytes, macrophages or mast cells. It is generally believed that the latter produce factors that maintain chronic inflammation and promote tumor growth, whereas lymphocytes may control cancer outcome, as evidenced in mouse models. In this study, we analyze data from large cohorts of human tumors, clearly establishing that infiltration of the primary tumor by memory T cells, particularly of the Th1 and cytotoxic types, is the strongest prognostic factor in terms of freedom from disease and overall survival at all stages of clinical disease. We review data suggesting that tertiary lymphoid structures adjacent to tumors and composed of mature dendritic cells (T and B cells organized as germinal centers) may be the site of an antitumor reaction. We propose an immune scoring based on the type, density and location of lymphocyte infiltrates as a novel prognostic factor, in addition to tumor node metastasis staging, to predict disease-free survival and to aid in decisions regarding adjuvant therapies in early stage human cancers.

The unmet medical need is the ability to determine which melanoma patients with node infiltration progress to metastisis and which would not based on a measure of the patients immune response. Current standard of practice is either to watch and monitor these patients or treat them with harsh interferon treatment.

As a multiplex IHC slide has the potential advantages of simultaneously identifying multiple biomarkers in a tissue section as opposed to single biomarker labeling in multiple slides. To support the pathologist with the slide interpretation process of multiplex IHC slides, digital pathology can serve to visually separate and quantitatively score the biomarkers for the immune cells, such as the different type of T-cells and B-cells. The following references disclose methods for assessing and/or scoring tissue, but are not adequate for multiplex slides: Manual tumor microenvironment assessment with CD3, CD8, CD45R0 and FoxP3: Paolo Ascierto, "The Medical Need for an Immune Scoring/

Profiling for Melanoma and Other Cancer Patients," Invited talk, Tucson Symposium, March 12-13, Tucson, Ariz., 2013; Manual/semi-automatic CD3/CD8 counting: Galon J Costes A Sanchez-Cabo F Kirilovsky A Mlecnik B Lagorce-Pages C Tosolini M Camus M Berger A Wind P Zinzindohoue F Bruneval P Cugnenc P H Trajanoski Z Fridman W H Pages F "Type, density, and location of immune cells within human colorectal tumors predict clinical outcome," Science 29; 313(5795):1960-4, 2006; Flow cytometry counting of CD8 and FoxP3: F. Stephen Hodi, "Recent Advances in Combinatorial Therapies," Invited talk, Tucson Symposium, March 12-13, Tucson, Ariz., 2013; Immune scoring from H&E: Sherene Loi, Nicolas Sirtaine, Fanny Piette, Roberto Salgado, Giuseppe Viale, Franc, oise Van Eenoo, Ghizlane Rouas, Prudence Francis, John P. A. Crown, Erika Hitre, Evandro de Azambuja, Emmanuel Quinaux, Angelo Di Leo, Stefan Michiels, Martine J. Piccart, and Christos Sotiriou, "Prognostic and Predictive Value of Tumor-Infiltrating Lymphocytes in a Phase III Randomized Adjuvant Breast Cancer Trial in Node-Positive Breast Cancer Comparing=the Addition of Docetaxel to Doxorubicin With Doxorubicin-Based Chemotherapy: BIG 02-98," Journal of Clinical Oncology 31(7), pp 860-867, 2013.

The technical hurdle has been to quantify the immune cell response on one slide and to incorporate the necessary immune markers. In order to fully understand the context of the patients current immune response to cancer, the tumor marker, B-cell, total T cell, cytotoxic T cell, and regulatory T cell populations should all be viewed together, and the scoring and interpretation must be automated and scalable to realistically function as a clinical concept.

Although there are methods to multiplex several markers, to our knowledge, there is no assay presented in either the research or commercial space which has incorporated these 5 markers in an assay, addresses this specific medical need, and includes a digital algorithm.

We developed a research prototype multiplexed assay and corresponding digital scoring algorithm based on clinical, biological, and statistical input. Our assay includes a tumor marker, as well as 4 immune markers.

Collectively, the immunological data (the type, density, and location of immune cells within the tumor samples) were found to be a better predictor of patient survival than the histopathological methods currently used to stage cancer. In colorectal cancer, the results were validated in two patient populations. This data supports the hypothesis that the adaptive immune response influences the behavior of human tumors. In situ analysis of tumor-infiltrating immune cells may therefore be a valuable prognostic tool in the treatment of colorectal cancer and other malignancies.

An image analysis algorithm and/or system has been developed that automatically computes an immune score from a set images of multiplex IHC slides and/or fluorescent stained slides. The image analysis algorithm involves a computer-implemented method for counting a number of types of cells in a single tissue specimen that has been stained with a multiplex assay, comprising: imaging the single tissue specimen that has been stained with the multiplex assay that includes lymphocyte markers CD3, CD8, CD20, FoxP3, and tumor detection markers; unmixing the image of single tissue specimen that has been stained with a multiplex assay into separate image channels for each marker of the multiplex assay; identifying regions of interest in each image channel based on intensity information in each channel, wherein regions of low intensity in each channel are removed, and regions of high intensity represent cell signals; generating a single surrogated image, wherein the surrogated image is a combination of the image channel information of all the lymphocyte markers; applying a cell detection algorithm, wherein the cell detection algorithm is a membrane finding algorithm or a nucleus finding algorithm; identifying features of the lymphocytes and combinations of lymphocytes in each image channel or image of combined channels, or a transformed image such as grayscale or absorbance image, or a surrogated image; training a classification algorithm based on features of known lymphocytes and lymphocyte combinations; applying the trained algorithm to features of the lymphocytes and combinations of lymphocytes in each image channel or in each image of combined channels, or in a transformed image such as grayscale or absorbance image, or in a surrogated image, that were identified to classify the detected cells as at least one of false positive cells, CD3 only T-cells, CD3 and CD8 T-cells, FP3 T-cells; and CD20 B-cells; counting a number of each different type of cell classified; generating a score of the tissue specimen, wherein the score is based on the number of each type of cell counted.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8(A)-(D) is (A) a photomicrograph similar to FIG. 7, unmixed into its component colors (B) and (D); and reassembled and pseudocolored in (C).

DETAILED DESCRIPTION

Figure 1A:
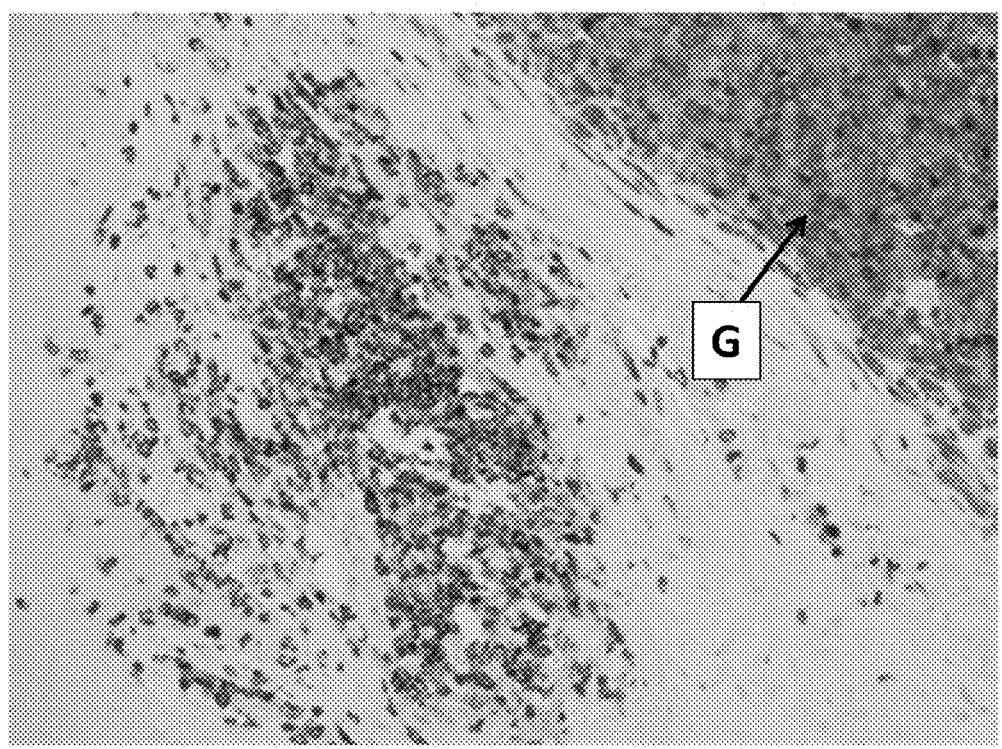
FIG. 1(A)-(B) are photomicrographs of a primary melanoma tissue (A) and (B) taken with (A) a 20× objective and (B) a 40× objective which shows a 5-plex stain with FoxP3 being detected in dark brown (exemplarily indicated by an arrow indicated with "DB" in FIG. 1(B)), CD8 detected in dark gray/black (exemplarily indicated by an arrow indicated with "DGB" in FIG. 1(B)), CD3 detected in blue (exemplarily indicated by an arrow indicated with "B" in FIG. 1(B)), CD20 detected in red/magenta (exemplarily indicated by an arrow indicated with "RM" in FIG. 1(B)) and S100 detected in green (exemplarily indicated by an arrow indicated with "G" in FIG. 1(A)), wherein (B) focuses on lymphocytic cells that can be seen to the left of the primary tumor.
Figure 1B:
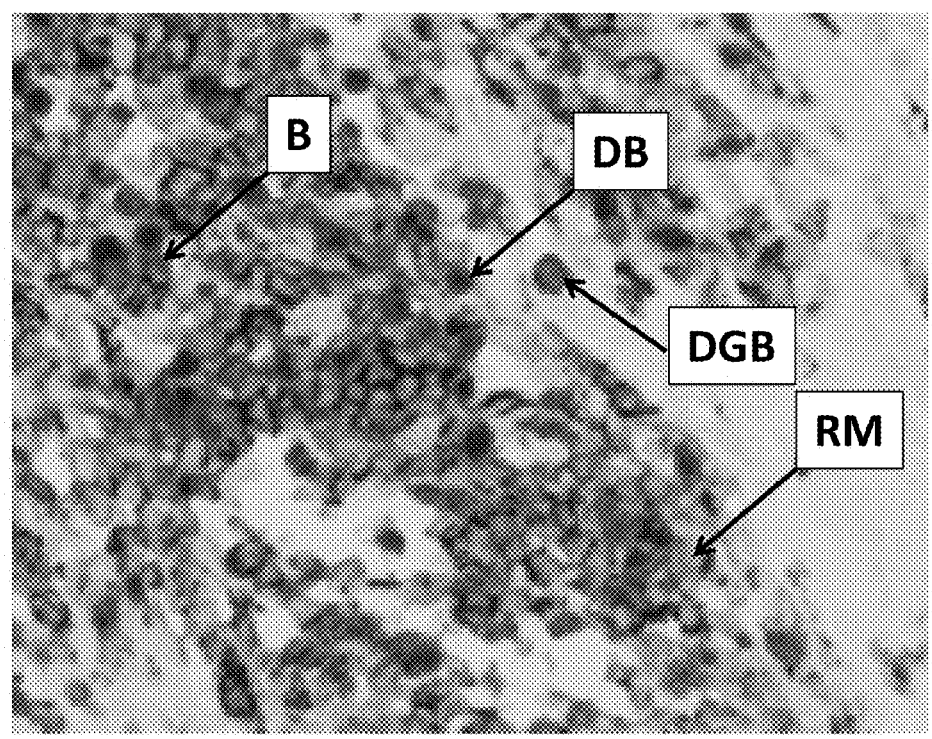
Figure 2A:
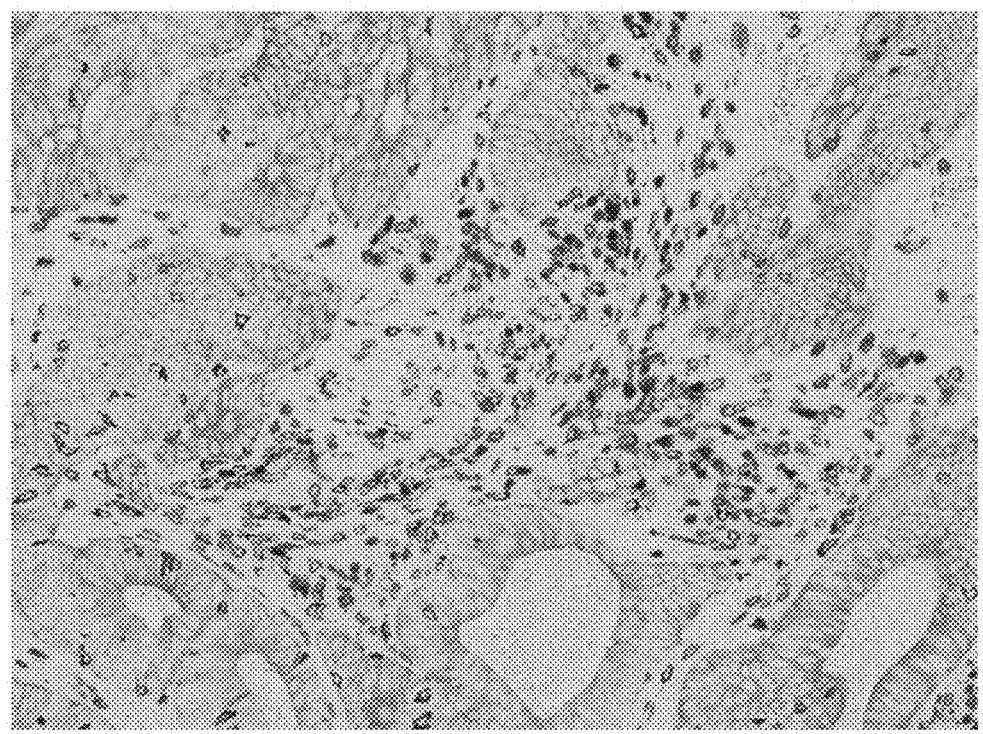
FIG. 2(A)-(B) are photomicrographs of a colon carcinoma tissue (A) and (B) taken with (A) a 20× objective and (B) a 40× objective which shows a 5-plex stain with FoxP3 being detected in dark brown (exemplarily indicated by an arrow indicated with "DB" in FIG. 2(B)), CD8 detected in dark gray/black (exemplarily indicated by an arrow indicated with "DGB" in FIG. 2(B)), CD3 detected in blue (exemplarily indicated by an arrow indicated with "B" in FIG. 2(B)), CD20 detected in red/magenta (exemplarily indicated by an arrow indicated with "RM" in FIG. 2(B)) and cytokeratin (OSCAR) detected in green (exemplarily indicated by an arrow indicated with "G" in FIG. 2(B)).
Figure 2B:
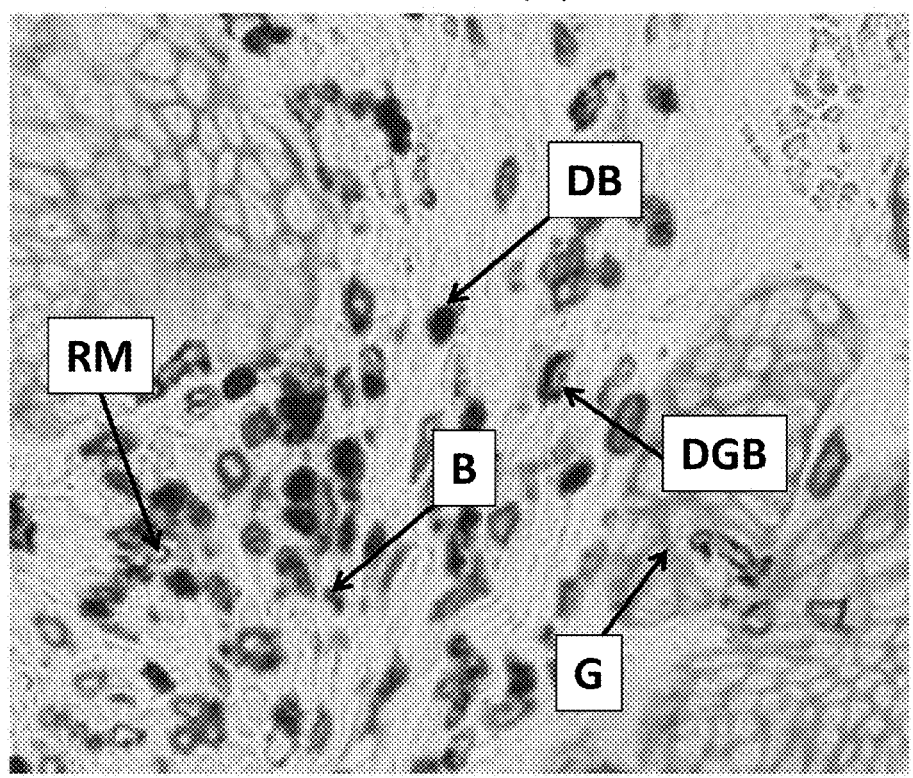
Figure 3:
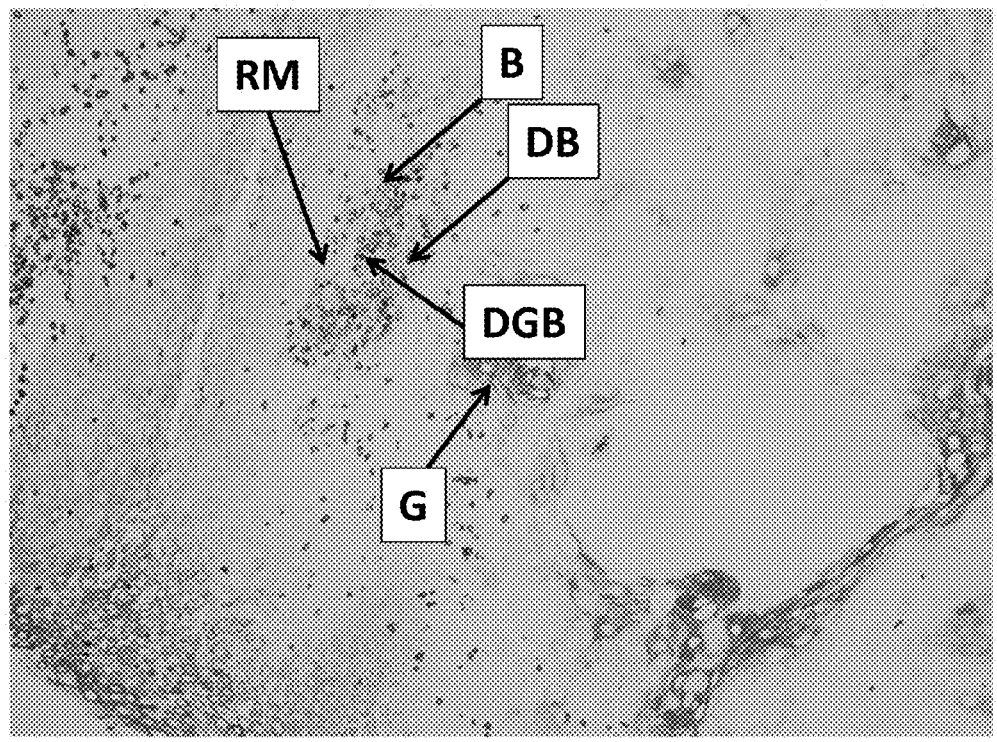
FIG. 3 is a photomicrograph of a tongue carcinoma tissue which shows a 5-plex stain with FoxP3 being detected in dark brown (exemplarily indicated by an arrow indicated with "DB"), CD8 detected in dark gray/black (exemplarily indicated by an arrow indicated with "DGB"), CD3 detected in blue (exemplarily indicated by an arrow indicated with "B"), CD20 detected in red/magenta (exemplarily indicated by an arrow indicated with "RM") and cytokeratin (OSCAR) detected in green (exemplarily indicated by an arrow indicated with "G").
Figure 4:
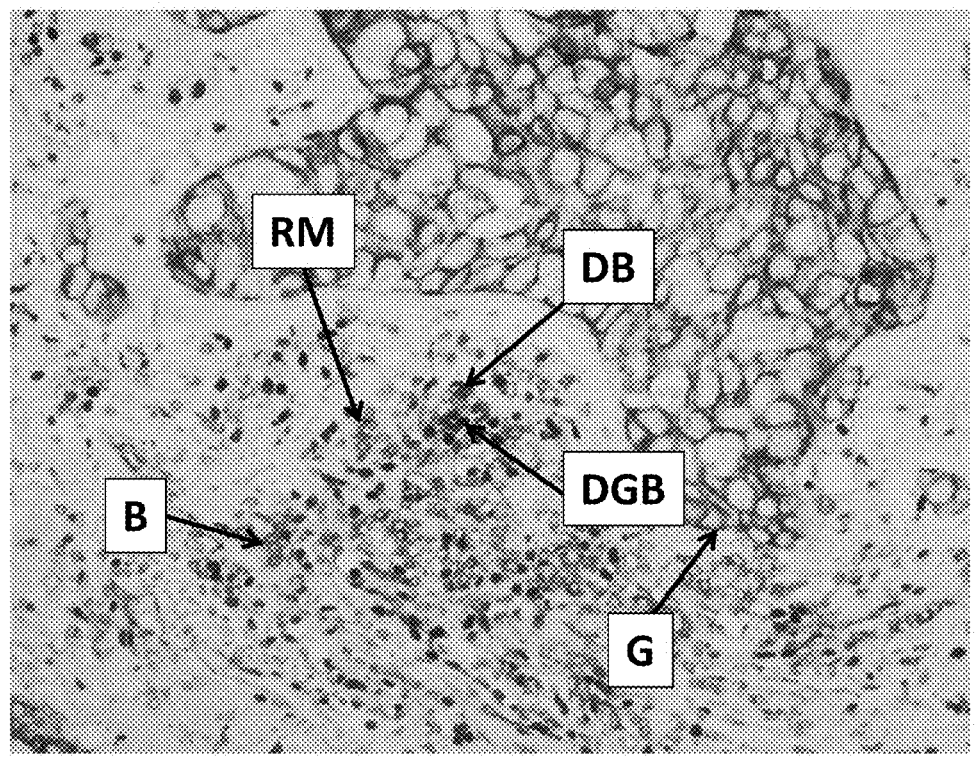
FIG. 4 is a photomicrograph of a lung adenocarcinoma tissue taken at a 20× objective which shows a 5-plex stain with FoxP3 being detected in dark brown (exemplarily indicated by an arrow indicated with "DB"), CD8 detected in dark gray/black (exemplarily indicated by an arrow indicated with "DGB"), CD3 detected in blue (exemplarily indicated by an arrow indicated with "B"), CD20 detected in red/magenta (exemplarily indicated by an arrow indicated with "RM") and cytokeratin (OSCAR) detected in green (exemplarily indicated by an arrow indicated with "G").
Figure 5:
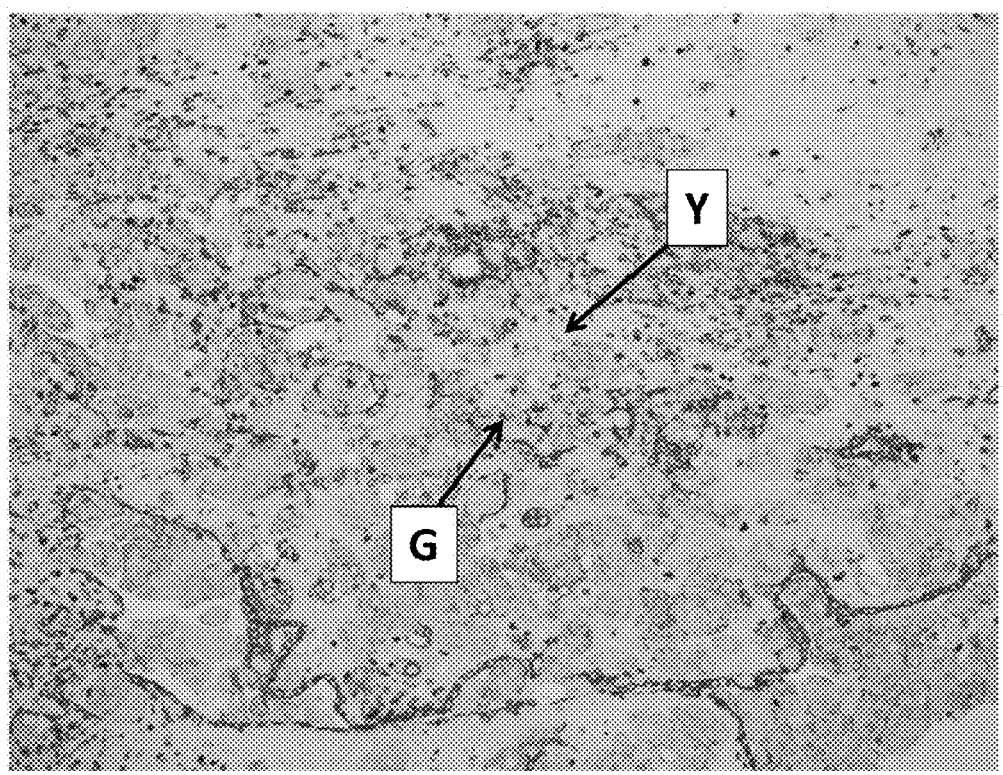
FIG. 5 is a photomicrograph (20× objective) of an ovarian adenocarcinoma tissue stained (5-plex) with antibodies for a cytokeratin tumor marker (yellow) (exemplarily indicated by an arrow indicated with "Y") and for infiltrating CD8+ cytotoxic T cells (green) (exemplarily indicated by an arrow indicated with "G"), further showing how the CD8 cells have infiltrated throughout the tumor.
Figure 6:
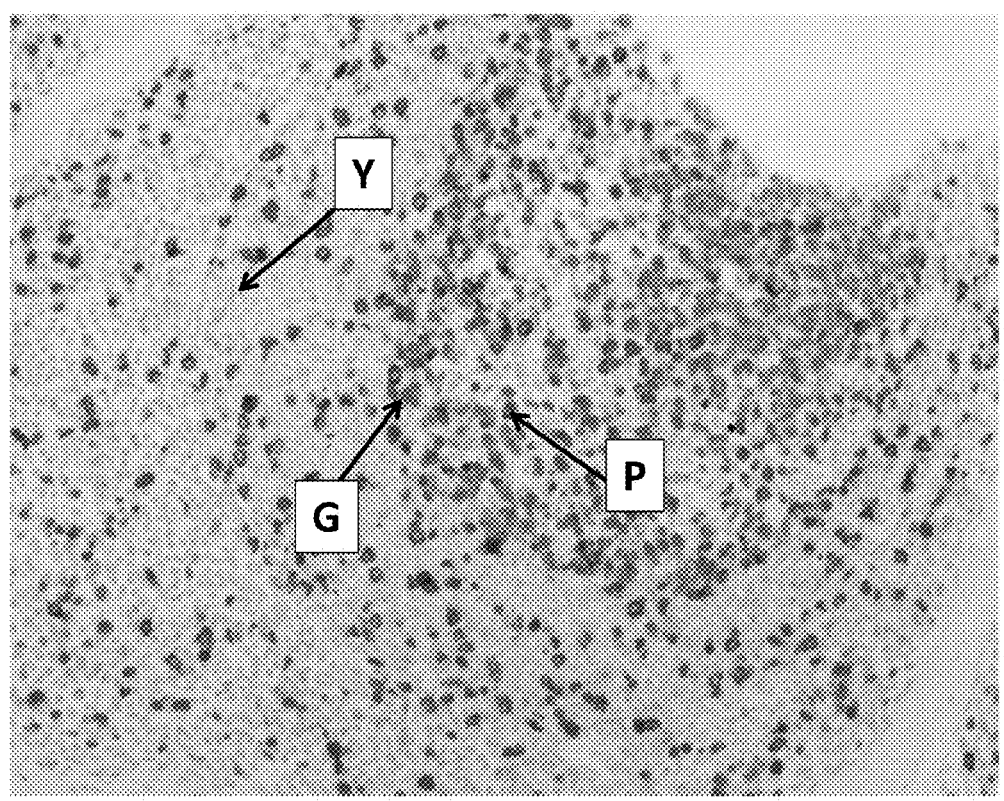
FIG. 6 is a photomicrograph of normal tonsil tissue stained with antibodies for proliferation marker Ki-67 (green) (exemplarily indicated by an arrow indicated with "G"), CD8+ T cells (purple) (exemplarily indicated by an arrow indicated with "P"), and CD3+ T cells (yellow) (exemplarily indicated by an arrow indicated with "Y"). This image confirms the localization of Ki-67+ cells in germinal centers with CD8 and CD3 cells, FoxP3 being detected in dark brown, and CD8 detected in the surrounding mantle zone. Magnification ×200.
Figure 7:
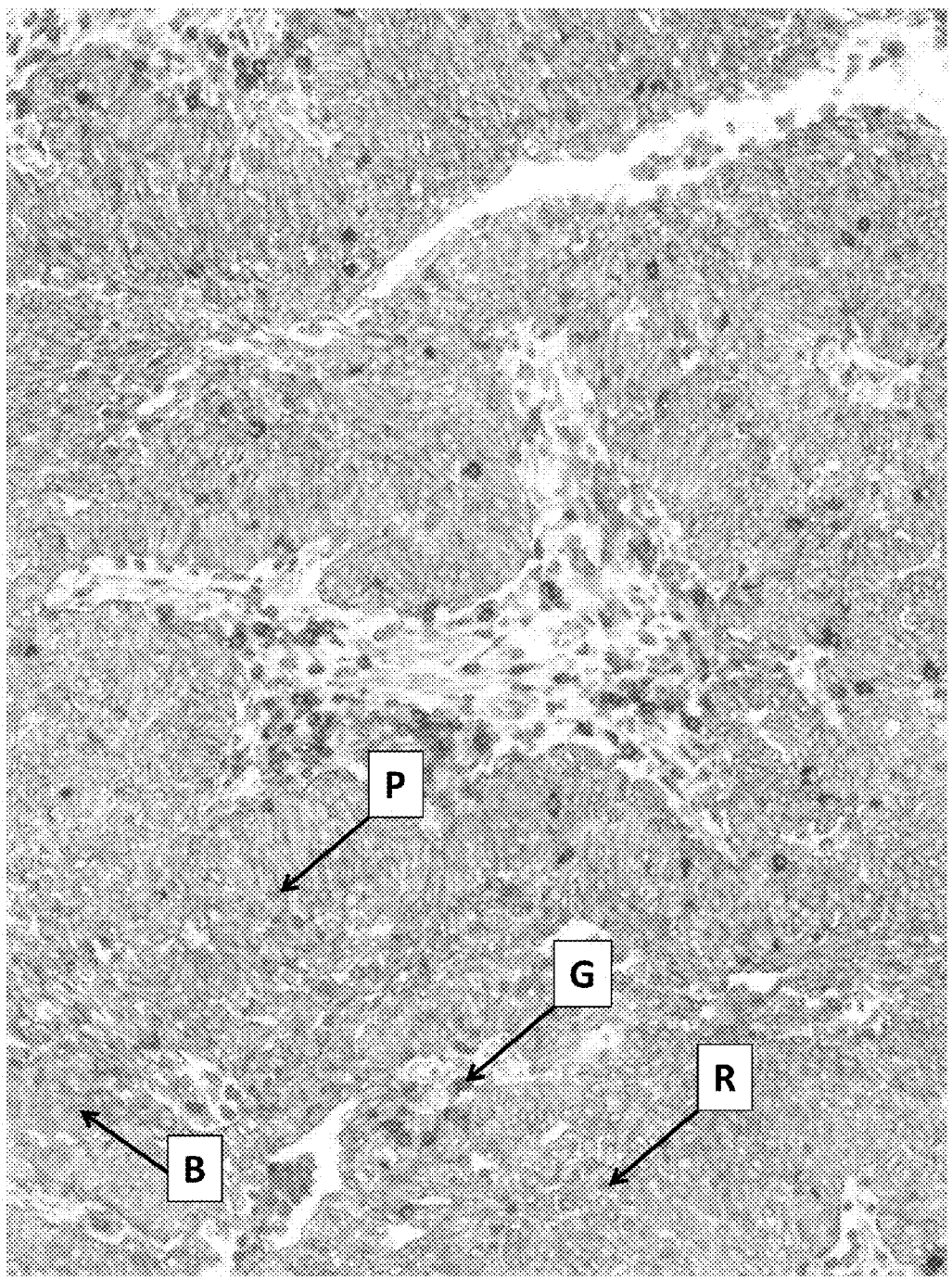
FIG. 7 is a photomicrograph (20× objective) of breast cancer tissue showing tumor in purple (exemplarily indicated by an arrow indicated with "P"), infiltrating CD8+ cells in green (exemplarily indicated by an arrow indicated with "G"), and CD68+ macrophages in blue (exemplarily indicated by an arrow indicated with "B"), and CD20 detected in red (exemplarily indicated by an arrow indicated with "R").

There is an unmet medical need to develop the ability to determine which melanoma patients with node infiltration progress to metastasis and which would not based on a measure of the patients immune response. Current standard of practice is either to watch and moniter these patients or treat them with harsh interferon treatment.

The technical hurdle has been quantifying an immune response that could be seen on one slide and that incorporates the necessary immune markers. In order to fully understand the context of the patient's current immune response to cancer, a tumor marker, B-cell, total T cell, cytotoxic T cell, and regulatory T cell populations should be viewed together, and the scoring and interpretation must be automated and scalable to realistically function as a clinical concept.

Although, there are methods to multiplex several markers, to our knowledge there is no assay presented in either the research or commercial space which incorporates these 5 markers in one assay, addresses this specific medical need, and includes a digital algorithm. Our assay includes a tumor marker, as well as 4 immune markers.

The multiplex assay, along with the image analysis algorithms, potentially provide a toolkit for the breast cancer and/or melanoma immune score computation. The final report generated by the computer may be used to support the clinical analysis of the patient's personal immune response and help guide further treatment, but further studies are needed to substantiate this hypothesis.

TIL

Immune cells infiltrating the tumor microenvironment (TILs) may either limit or promote tumor progression. Increasing evidence demonstrates that the number, type and location of TILs in primary tumors may have a prognostic role. These observations have led to the development of potential new scoring systems derived from the immune context in tissue and based on the identification and evaluation of specific lymphocyte populations. We explored the potential prognostic value of cells positive for a combination of CD3, CD8, CD20, and FOXP3 as an 'Immunoscore' for melanoma patients which would utilize widely accessible, standardized technology.

We developed a research prototype multiplexed assay and corresponding digital scoring algorithm based on clinical, biological, and statistical input.

A multiplex IHC slide has the potential advantage of simultaneously identifying multiple biomarkers in a single tissue section as opposed to single biomarker labeling in multiple slides, thereby demonstrating much more information within one small piece of tissue. With this purpose in mind, a multiplex assay has been developed to provide an immune score for patients with breast cancer and melanoma, along with other tumor types. To support pathologists with the slide interpretation process, digital pathology can serve to visually separate and quantitatively score the biomarkers for the immune cells, such as the different types of TILs.

CD3

CD3 is the "universal marker" for T cells in general. Further analysis (staining) must be done to identify the type of T cell, e.g. regulatory or cytotoxic T cell. An analysis of CD3+ T cell numbers is a good indication of immune response.

CD8

CD8 is a specific marker for cytotoxic T lymphocytes. These are the effector cells that actually "kill" tumor cells. They act by direct contact to introduce the digestive enzyme granzyme B into the tumor cell cytoplasm, thereby killing it. Therefore, it is important not only to know their overall numbers but also their localization relative to the tumor itself. Only those cells in direct contact with tumor cells will be effective in cell killing.

CD20

CD20 is a marker for antibody-producing B cells. As such, it is an indication of a more fully developed (mature) immune response. The total numbers and localization of these antibody-producing effector cells may be of importance.

FoxP3

FoxP3 is a nuclear transcription factor that is the most specific marker for regulatory T cells (so-called Tregs). Tregs function to moderate the immune response. Presumably, the presence of Tregs would indicate an inhibitory immune response to a tumor.

Tumor Markers

In epithelial tumors (carcinomas), cytokeratin staining identifies tumor cells as well as the normal epithelium. This information, together with the fact that tumor cells abnormally overexpress the cytokeratins compared to normal epithelial cells, allows one to identify tumor vs. normal tissue. For melanoma tissue of neuroectodermal origin, the S100 biomarker serves a similar purpose.

Primary Staining/Blueing/Counterstaining

In illustrative embodiments, the method includes applying a chromogenic reagent so that the sample is specifically stained. In one embodiment, specifically staining includes the application of a primary stain that selectively stains portions of the sample through adhesion associated with hydrophobicity, intercalation, or other non-recognition associations. For example, hematoxylin and eosin staining (H&E staining) is well known in the art. Reference is made to U.S. Published Patent Application 2008/0227143, which is hereby incorporated by reference for disclosure related to hematoxylin and primary staining. H&E staining is used for the evaluation of cellular morphology and is the primary tool for pathologically diagnosing cancer.

Detection

The method includes applying an immunohistochemical (IHC) binding reagent or an in situ hybridization (ISH) binding reagent so that the IHC binding reagent or the ISH binding reagent contact the sample. ISH can be used to diagnose the presence of a genetic abnormality or condition, or over- or under-expression from the norm. For example, ISH may be used to detect gene amplification, deletion, or translocation of genes related to a particular disease. ISH is also useful in the diagnosis of infectious diseases as it allows detection of microbial and viral sequences within infected cells. IHC includes antibodies specifically binding epitopes of interest. The epitopes, also referred to as antigens or antigenic sequences, are portions of proteins that have been established as a marker of clinical interest. For example, the epitope may be a mutated form of a protein, a protein-protein binding site, or a normal protein that is expressed at a concentration either higher or lower than normal, such as in a control sample. Detection and/or quantification of epitopes in various biological samples have been used for a vast number of clinical purposes.

Both IHC and ISH involve a specific recognition event between a nucleic acid probe (ISH) or an antibody (IHC) and a target within the sample. This specific interaction labels the target. The label can be directly visualized (direct labeling) or indirectly observed using additional detection chemistries. Chromogenic detection, which involves the deposition of a chromogenic substance in the vicinity of the label, involves further detection steps to amplify the intensity of the signal to facilitate visualization. Visualization of the amplified signal (e.g. the use of reporter molecules) allows an observer to localize targets in the sample.

Chromogenic detection offers a simple and cost-effective method of detection. Chromogenic substrates have traditionally functioned by precipitating when acted on by the appropriate enzyme. That is, the traditional chromogenic substance is converted from a soluble reagent into an insoluble, colored precipitate upon contacting the enzyme. The resulting colored precipitate requires no special equipment for processing or visualizing. Table 1 is a non-exhaustive list of chromogen systems useful within the scope of the present disclosure:

TABLE 1

Chromogenic detection reagents.

| Abbr. | Name | Color | Enzyme |
| --- | --- | --- | --- |
| DAB | 3,3'-diamino-benzidine + $H_2O_2$ | brown - black | peroxidase |

TABLE 1-continued

Chromogenic detection reagents.

| Abbr. | Name | Color | Enzyme |
| --- | --- | --- | --- |
| AEC | 3-amino-9-ethyl-carbazole + $H_2O_2$ | red | peroxidase |
| CN | 4-chloro-1-naphthol + $H_2O_2$ | blue | peroxidase |
| BCIP/NBT | 5-bromo-4-chloro-3-indolyl-phosphate + nitroblue tetrazolium | indigo - black | alkaline phosphatase |
| FAST RED | 4-chloro-2-methyl-benzenediazonium + 3-hydroxy-2-naphthoic acid 2,4-dimethylanilide phosphate | red | alkaline phosphatase |
| FAST BLUE | Naphthol AS-MX phosphate disodium salt + fast blue BB salt hemi(zinc chloride) salt | blue | alkaline phosphatase |
| FUCHSIN | Naphthol AS-BI + New Fuchsin | red | alkaline phosphatase |
| NBT | nitroblue tetrazolium + phenazine methosulfate | blue - purple | dehydrogenase |
| ALK GOLD† | 3-methyl-1-phenyl-1H-pyrazol-5-yl dihydrogen phosphate + fast blue BB | yellow - gold | alkaline phosphatase |

Table 1, while not exhaustive, provides insight into the varieties of presently available chromogenic substances (†WO2012/024185, Kelly et al. "Substrates for Chromogenic detection and methods of use in detection assays and kits").

A key advancement to the present invention is the use of tyramide-chromogen conjugates that allow deposition and covalent binding of here-to-fore novel chromogens of novel color schemes. This covalent binding also has the added advantage of being able to dehydrate the specimen slides in a series of increasing concentrations of alcohol solutions followed by xylene and mounting in a hardened plastic for permanent preservation. This results in improved morphology and resolution of staining compared to other chromogen dye staining techniques that employ dyes that are extracted by this conventional histological processing.

One aspect of the present disclosure is that the chromogen conjugates may be configured to absorb light more selectively than traditionally available chromogens. Detection is realized by absorbance of the light by the signaling conjugate; for example, absorbance of at least about 5% of incident light would facilitate detection of the target. In other darker stains, at least about 20% of incident light would be absorbed. Non-uniform absorbance of light within the visible spectra results in the chromophore moiety appearing colored. The signaling conjugates disclosed herein may appear colored due to their absorbance; the signaling conjugates may appear to provide any color when used in the assay, with certain particular colors including red, orange, yellow, green, indigo, or violet depending on the spectral absorbance associated with the chomophore moiety. According to another aspect, the chromophore moieties may have narrower spectral absorbances than those absorbances of traditionally used chromogens (e.g. DAB, Fast Red, Fast Blue). In illustrative embodiments, the spectral absorbance associated with the first chromophore moiety of the first signaling conjugate has a full-width half-max (FWHM) of between 30 nm and 250 nm, between 30 nm and 150 nm, between 30 nm and 100 nm, or between 20 nm and 60 nm.

Narrow spectral absorbances enable the signaling conjugate chromophore moiety to be analyzed differently than traditional chromogens. While having enhanced features compared to traditional chromogens, detecting the signaling conjugates remains simple. In illustrative embodiments, detecting comprises using a brightfield microscope or an equivalent digital scanner. The narrow spectral absorbances enable chromogenic multiplexing at a level beyond the capability of traditional chromogens. For example, traditional chromogens are somewhat routinely duplexed (e.g. Fast Red and Fast Blue, Fast Red and Black (silver), Fast Red and DAB). However, triplexed or three-color applications, or greater, are atypical, as it becomes difficult to discern one chromophore from another, especially when they overlap or co-localize. In illustrative embodiments of the presently disclosed technology, the method includes detecting from at least two, and up to six or more, different targets using different signaling conjugates or combinations thereof. In one embodiment, illuminating the biological sample with light comprises illuminating the biological sample with a spectrally narrow light source, the spectrally narrow light source having a spectral emission with a second full-width half-max (FWHM) of between 30 nm and 250 nm, between 30 nm and 150 nm, between 30 nm and 100 nm, or between 20 nm and 60 nm. In another embodiment, illuminating the biological sample with light includes illuminating the biological sample with an LED light source. In another embodiment, illuminating the biological sample with light includes illuminating the biological sample with a filtered light source.

Reference is made to US20130260379 which is incorporated by reference herein, in its entirety. Reference is also made to U.S. Appl. Ser. No. 61/831,552 which is incorporated by reference herein, in its entirety.

Automated Scoring

Algorithms

In one exemplary embodiment, the subject disclosure is a non-transitory computer-readable medium for storing computer-executable instructions that are executed by a processor to perform operations including training an algorithm, computing a score, and unmixing. In another exemplary embodiment, the subject disclosure is a system for digital pathology including a processor and a memory coupled to the processor, the memory to store computer-executable instructions that, when executed by the processor, cause the processor to perform operations, including training an algorithm, computing a score, and unmixing.

The present invention includes an image analysis system that automatically computes a score, for example, an immune score, for a multiplex assay (e.g., a set of multiplex IHC slides) or fluorescent stained slide or slides. The image analysis system includes software modules and algorithms, that include computer executable instructions that are executed by, for example, a processor, for the purpose of analyzing images of tissue stained with a multiplex assay, and for generating a score based off of the analysis. The image analysis system is able to identify multiple biomarkers in the same biological specimen, for example a single tissue specimen, and is applicable to a multiplex assay for any tissue type.

For exemplary purposes, the image analysis algorithm of the present invention is described in connection with cancerous tissue slides that are stained by a multiplex assay. As an example of implementation of the image analysis algorithm of the present invention, breast tissue slides are analyzed. In an exemplary embodiment of the present invention, stained tissue slides are imaged and/or scanned, and the corresponding color images are generated, and input into the image analysis system. Alternatively, the images are obtained from a source.

The present invention is applicable to brightfield and fluorescence images, and a microscopy system (e.g., a brightfield microscopy system) or a scanner is utilized for imaging or scanning the slides and obtaining the brightfield images. To generate multi-spectral images, a multi-spectral imaging system (such as a fluorescent microscope or scanner (e.g., a whole slide scanner) is used to obtain the multi-spectral fluorescent images.

To analyze the generated or obtained images, the image analysis algorithm and/or system of the present invention includes a color unmixing algorithm, which may be included in an unmixing module, that identifies the individual constituent dyes for the biomarkers and the proportions in which they appear in the color images. The unmixing operations may be performed in accordance with the unmixing method disclosed in U.S. Provisional Application No. 61/830,620, filed Jun. 3, 2013, and entitled IMAGE ADAPTIVE PHYSIOLOGICALLY PLAUSIBLE COLOR SEPARATION, the disclosure of which is incorporated herein by reference in its entirety. Based on the separated image channels for each marker, detection algorithms are developed to automatically identify different combination of T and B lymphocytes with respect to each of the differentiating IHC markers. For example, different T-cell markers might co-localize and create different combination of the stain amounts. Additionally, a tumor marker, for example a cytokeratin marker (e.g., Oscar), may also be included in the assay to identify the tumor, intratumoral and/or peritumoral regions to get the tissue context (for example, to identify the nuclei and the tumor regions). In an exemplary embodiment, image analysis is performed, after unmixing, to identify, quantify and/or generate a score for a biomarker, for example, Oscar, CD3, CD8 and FoxP3 markers. In an exemplary embodiment of the present invention, the score for each marker may be reported, along with the tissue context information, as output.

Figure 9:
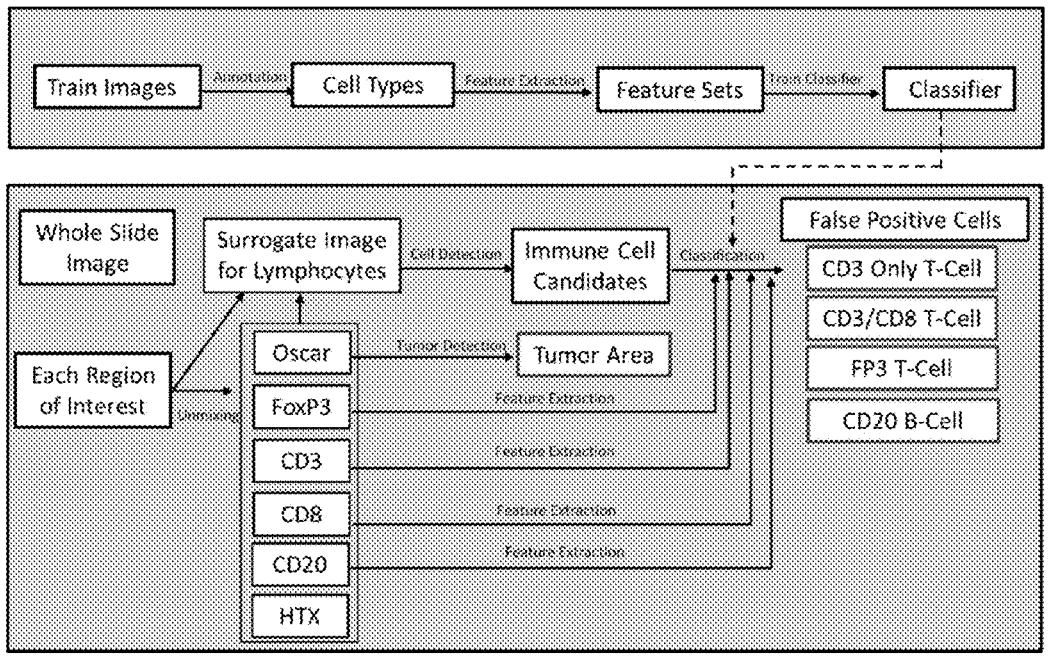
FIG. 9 is a schematic illustrating a Scoring Algorithm Workflow in accordance with the present disclosure.

FIG. 9 illustrates the workflow of an image analysis method and system of the present invention. FIG. 9 shows an example implementation of an image analysis method, in accordance with the present invention, that depicts details associated the image analysis method being applied to breast cancer immune score computation.

The image analysis method of the present invention involves a training stage, which may be incorporated into a training stage module. In the training stage identification for different type of lymphocytes as well as the examples of false positive cells may be performed first, for each marker. For example, in FIG. 9, the seeds within the cells (e.g., true positive T-cells) and seeds outside the cells (e.g., false positive T-cells) are manually annotated, after the automatic detection.

Next, one or more feature extraction algorithms, in accordance with the present invention, which may be incorporated in a feature extraction module, is applied to an image patch around the seed to obtain a feature set for each type of cells (e.g., CD3 cells, CD8 cells and CD20 cells). The features are extracted from different image channels, for example, the RGB channels of the image, the absorbance space, the unmixed channels and the grayscale image. Here different feature extraction algorithms can be used. For example, as shown in FIG. 9, dictionary learning can be applied to build a codebook for the different cell appearances.

In an exemplary embodiment of the present invention, a classification algorithm, which may be included in a classification module, may be trained to classify different types of cells present in an image, for example, an image of tissue stained with a multiplex assay. In exemplary embodiments of the present invention different classification algorithms, for example, SVM, Random Forest and Boosting etc. algorithms may be applied. In an exemplary embodiment of the present invention, an SVM algorithm is utilized in the classification algorithm, as shown in FIG. 9 to associate a feature with a label for the feature.

In the testing stage and/or implementation stage, where the classification algorithm, in accordance with the present invention, is applied, the whole slide image, or portion thereof, is input into the image analysis method/system of the present invention. For each region of interest in the whole slide image, or portion thereof, the following steps of unmixing, removing tumor-related noise, generating a surrogated image, ring or blob detecting (e.g., to find lymphocytes with membrane markers), feature extracting, classifying, and counting of types of cells or lymphocytes are applied. A surrogated image of lymphocytes (i.e., an image that contains all the T-cells) may be obtained first. By doing so, we can first detect all the T-cells and then use the classification algorithm to identify the cell types. To generate the surrogated image, a log transform is utilized to convert the RGB image into absorbance space, and then the Oscar channel may be utilized to remove the noise (tumor cells) as shown in FIG. 9, since we are not detecting the tumor cells. In an exemplary embodiment of the present invention, the Oscar channel information, including the tumor cell information is saved in a memory in order to count the tumor cells. A surrogated image is utilized to do detection, instead of each unmixed channel, because unmixing multiplex assays, for example assays having five or more markers, may not be reliable due to the huge color variation across the image. In exemplary embodiments of the present invention, a combined image of some other sort may be utilized, for example, a transformed image (e.g., an absorbance image or grey scale image) or an image that combines various channels. Then the input image (e.g., the RGB image) may be unmixed into different channels of biomarkers, for example, the Oscar, FoxP3, CD3, CD8, HTX and CD20 channels.

Figure 10:
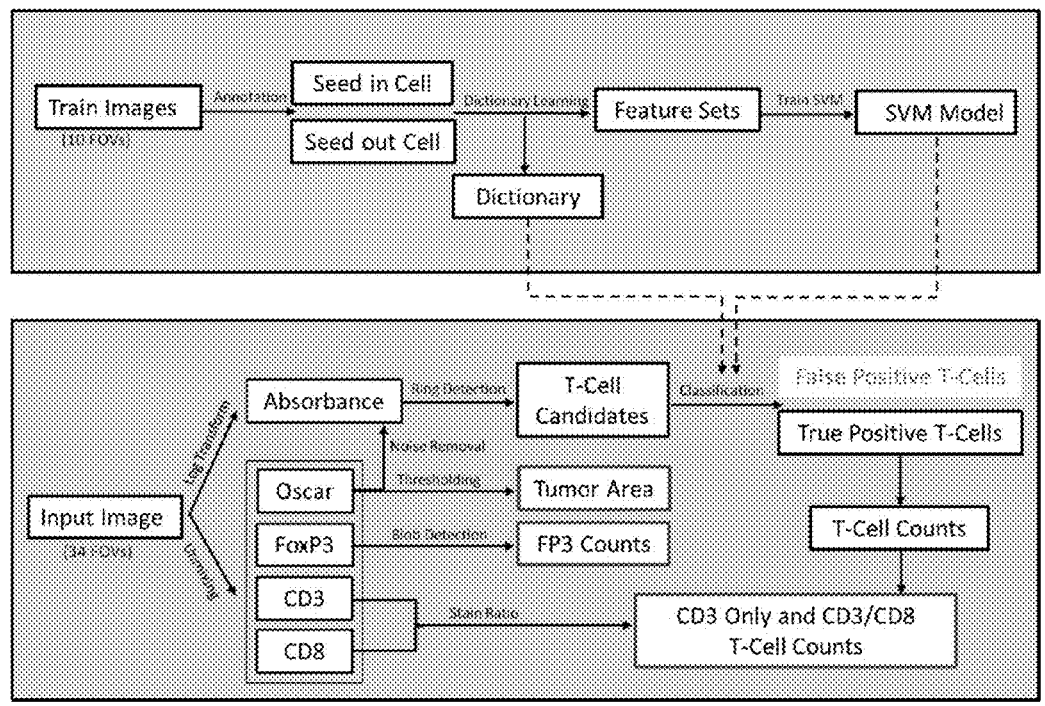
FIG. 10 is a schematic illustrating an example implementation of the Scoring Algorithm in accordance with the present invention.

The cell detection algorithm (e.g., corresponding to the ring detector in FIG. 10), may be included in a cell detection module, and is applied to the surrogated image to detect the lymphocytes. In an exemplary embodiment of the present invention, the ring shape of the cell detection algorithm provides for capturing ring shape membrane markers (e.g. all the possible T-cell candidates and may include false positive detections). We use the absorbance image with Oscar correction as the surrogated image in the implementation (FIG. 9) to detect the ring shape membrane markers. In the implementation stage, a cell detection algorithm that is very sensitive, is desirable, e.g., an algorithm that captures all possible cells and may include the false positive detections. In an exemplary embodiment of the present invention, a ring detector may be applied to the surrogate image to detect the membrane markers, which are utilized to identify cells. FIG. 10 illustrates a simple example of the ring detector. It should be understood by one skilled in the art that other and different types of cell detection algorithms may be applied to an image (surrogate or otherwise) to detect cells.

A classifier, for example, the classifier learned or generated from the training stage, may be then used to classify all the cell candidate seeds between categories, such as false positive cell, CD3 only T-cell, CD3/CD8 T-cell, FP3 T-cell and B-cell.

In exemplary embodiments, the information from CD3, CD8, FP3 and CD20 channels, for example information regarding the colors and shapes of cells in the respective channels, may also be used as a feature for classification. FIG. 9 illustrates an example of implementation of the dictionary learning algorithm. In this example, (1) a learned appearance feature, for example, the shape of the cell, which was obtained from the local patch around the seed, is utilized to distinguish between true positive and false positive lymphocytes and (2) the stain amount feature is utilized to classify, for example, the CD3-only and CD3/CD8 T-cells.

In particular, for each detected true positive T-cell in a surrogate image, the CD3 and CD8 pixels around the neighborhood of the T-cell, from CD3 and CD8 unmixed channels may be obtained, and the ratio of the two stains is computed to classify between (1) CDs positive and CD8 positive cells and (2) CD3 positive only cells. In an exemplary embodiment of the present invention, if (number of CD8 pixels)/(number of CD3 pixels)<threshold, the cell identified in the surrogate image is labeled as CD3 only cell, otherwise it is labeled as CD3/CD8 cell.

To identify nuclei we evaluate the nuclear marker channel, for example, the FoxP3 channel image, as FoxP3 is the nuclear marker. We apply the blob detection algorithm, which may be included in a blob detection module, in the FoxP3 channel to find the FoxP3 nuclei. In an alternative embodiment of the present invention, a radial symmetry algorithm, which may be included in a radial symmetry module, may be utilized to detect nuclei. However, it should be understood by one of ordinary skill in the art that other blob detection methods may be accomplished utilizing, for example, a circular transform.

To identify the tumor region, the Oscar channel is utilized. In exemplary embodiments of the present invention, region detection algorithms may be used to identify the tumor regions. In the implementation shown in (FIG. 11), an Otsu thresholding method is applied to Oscar channel to find the tumor region. The Otsu thresholding method identifies the tumor region by a process that finds the best threshold for the foreground and background. The Oscar channel is also utilized to remove the noise associated with the tumor region. The Oscar channel is also utilized to remove the ring shape tumor cytoplasmic markers. As cytoplasmic markers sometimes create ring shape appearance, we need to remove those regions first before applying ring detection. We note that the order of the steps of the image analysis algorithms, methods, and/or systems of the present invention may vary.

Figure 11A:
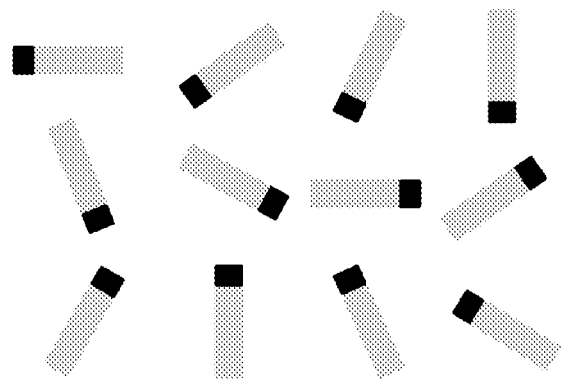
FIG. 11(A)-(B) is a schematic illustrating a filter bank (A) and ring detector (B) in accordance with the present invention.
Figure 11B:
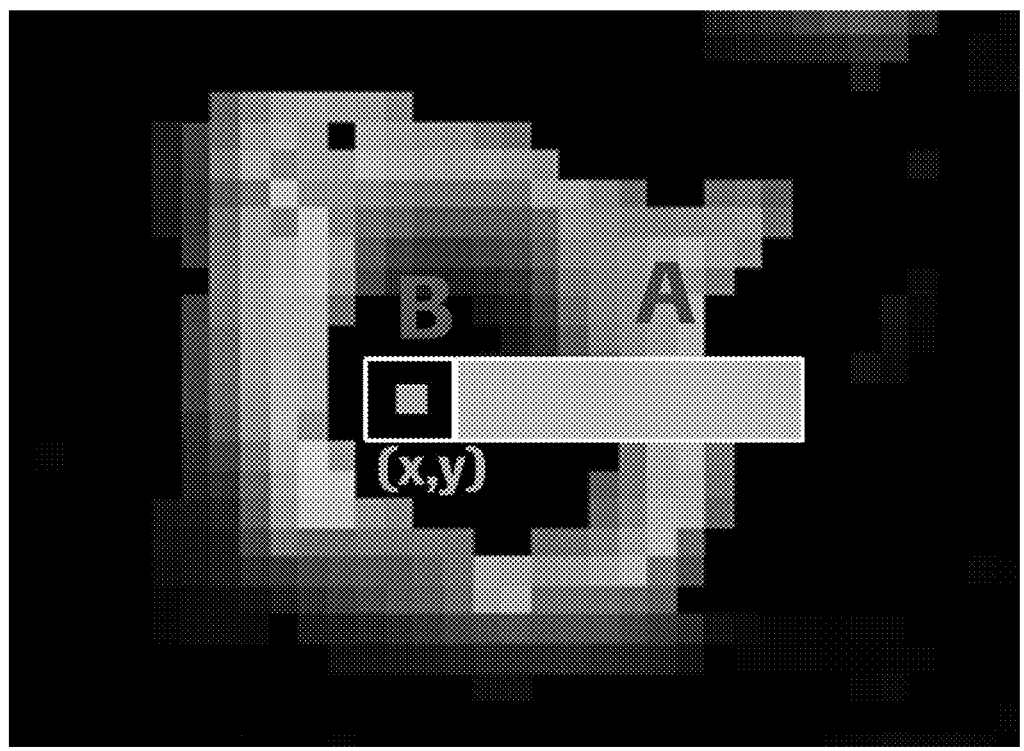

FIG. 11(B) illustrates an exemplary ring detector, in accordance with the present invention, that may be utilized for lymphocyte detection in our implementation. To implement a ring detector, a filter bank, i.e., a set of masks containing 12 directions, as shown in FIG. 11(A), may be built. The black region denote pixels of −1 which cover the center of the ring and the gray region corresponds to pixels of 1 covering the boundary of the ring, so that when this mask is convolved with the image we obtain the intensity difference between the ring boundary and the center. In this example, the width of the filter is 3 pixels, the length of black region is 5 pixels and the length of the gray region is 10 pixels. The parameters, including, for example, the number of directions, width and length of the filter are adjustable, for example, to correspond to the different cell sizes for which detection is desired. As shown in FIG. 11(B), for each location (x,y) in the image, the vote V(x,y)=V(x,y)+[sum(I (A))−sum(I(B))] is computed. The vote corresponds to the intensity value difference of total pixel intensities within the black region of the filter and the gray region of the filter. This vote is accumulated at (x,y) along 12 directions at the center of the ring. Note that 12 is just an example number of directions and different number can be used. In exemplary embodiments of the present invention, multi-scale detection (i.e., different sizes of the ring) may be utilized to capture cells at different sizes by tuning the parameters of the filter.

One embodiment relates to a user interface and functionalities associated with an image analysis system and/or method in accordance with the present invention. The user interface provides the following functionalities:

A load image feature that allows for loading the FOVs or whole slide images via the "Load Data Dir" button. A detect tissue region feature that allows for detection of the lymphocytes and tumor regions and/or display of the detection results by clicking, for example, the file name in the "File List" panel.

A cell modification feature that allows the user to modify the cell detection results, add and/or delete annotations. In an exemplary embodiment of the present invention, a user may first select the type of cell to modify from the popup list, then click the "Modify Cell" button to start editing, and a left click of the mouse corresponds to, for example, being able to delete a seed and a right click of the mouse corresponds, for example, to being able to add a seed. After edits have been made, activation of the "Enter" key on keyboard indicates that editing is complete.

A tumor modification feature allows the user to modify the tumor detection results. In an exemplary embodiment of the present invention by clicking the "Add Region" and "Remove Region" icons or regions of a user interface, a user may to start draw a polygon and a double left click of the mouse, for example, allows a user to indicate that the drawing of the polygon is complete.

A save modification feature allows a user, via activation of a "Save Modification" button to save the modification.

A create final report feature allows a user to create a final report that includes, for example, the immune score, which is based on a number of one or more cell types. For example, a user may click the "Get Report" button or region of the user interface to generate the final report. It should be understood by one of ordinary skill in the art that buttons, icons, and regions of the screen may be utilized to activate features, and can all be utilized as alternatives to the other.

An exemplary embodiment of a computer system for use in accordance with the present disclosure may include any number of computer platforms or multiple types of computer platforms, such as workstations, personal computers, servers, hand-held devices, multi-processor systems, microprocessor-based or programmable consumer electronics, network PCs, minicomputers, mainframe computers or any other present or future computer. An exemplary embodiment may also be practiced in distributed computing environments where tasks are performed by local and/or remote processing devices that are connected (by, for example, hardwired connections, wireless connections, or a combination thereof), in a communications network. In a distributed computing environment, program modules may be located in both local and remote computer storage media including memory storage devices. It will, however, be appreciated by one of ordinary skill in the art that the aforementioned computer platforms as described herein are specifically configured to perform the specialized operations of the described invention and are not considered general purpose computers.

Computers typically include known components, such as a processor, an operating system, system memory, memory storage devices, input-output controllers, input-output devices, and display devices. It will also be understood by those of ordinary skill in the relevant art that there are many possible configurations and components of a computer and may also include cache memory, a data backup unit, and many other devices. Examples of input devices include a keyboard, a cursor control devices (e.g., a mouse), a microphone, a scanner, and so forth. Examples of output devices include a display device (e.g., a monitor or projector), speakers, a printer, a network card, and so forth. Display devices may include display devices that provide visual information, this information typically may be logically and/or physically organized as an array of pixels. An interface controller may also be included that may comprise any of a variety of known or future software programs for providing input and output interfaces. For example, interfaces may include what are generally referred to as "Graphical User Interfaces" (often referred to as GUI's) that provide one or more graphical representations to a user. Interfaces are typically enabled to accept user inputs using means of selection or input known to those of ordinary skill in the related art. The interface may also be a touch screen device. In the same or alternative embodiments, applications on a computer may employ an interface that includes what are referred to as "command line interfaces" (often referred to as CLI's). CLI's typically provide a text based interaction between an application and a user. Typically, command line interfaces present output and receive input as lines of text through display devices. For example, some implementations may include what are referred to as a "shell" such as Unix Shells known to those of ordinary skill in the related art, or Microsoft Windows Powershell that employs object-oriented type programming architectures such as the Microsoft .NET framework.

Those of ordinary skill in the related art will appreciate that interfaces may include one or more GUI's, CLI's or a combination thereof.

A processor may include a commercially available processor such as a Celeron, Core, or Pentium processor made by Intel Corporation, a SPARC processor made by Sun Microsystems, an Athlon, Sempron, Phenom, or Opteron processor made by AMD Corporation, or it may be one of other processors that are or will become available. Some embodiments of a processor may include what is referred to as multi-core processor and/or be enabled to employ parallel processing technology in a single or multi-core configuration. For example, a multi-core architecture typically comprises two or more processor "execution cores". In the present example, each execution core may perform as an independent processor that enables parallel execution of multiple threads. In addition, those of ordinary skill in the related will appreciate that a processor may be configured in what is generally referred to as 32 or 64 bit architectures, or other architectural configurations now known or that may be developed in the future.

A processor typically executes an operating system, which may be, for example, a Windows type operating system from the Microsoft Corporation; the Mac OS X operating system from Apple Computer Corp.; a Unix or Linux-type operating system available from many vendors or what is referred to as an open source; another or a future operating system; or some combination thereof. An operating system interfaces with firmware and hardware in a well-known manner, and facilitates the processor in coordinating and executing the functions of various computer programs that may be written in a variety of programming languages. An operating system, typically in cooperation with a processor, coordinates and executes functions of the other components of a computer. An operating system also provides scheduling, input-output control, file and data management, memory management, and communication control and related services, all in accordance with known techniques.

System memory may include any of a variety of known or future memory storage devices that can be used to store the desired information and that can be accessed by a computer. Computer readable storage media may include volatile and non-volatile, removable and non-removable media implemented in any method or technology for storage of information such as computer readable instructions, data structures, program modules, or other data. Examples include any commonly available random access memory (RAM), read-only memory (ROM), electronically erasable programmable read-only memory (EEPROM), digital versatile disks (DVD), magnetic medium, such as a resident hard disk or tape, an optical medium such as a read and write compact disc, or other memory storage device. Memory storage devices may include any of a variety of known or future devices, including a compact disk drive, a tape drive, a removable hard disk drive, USB or flash drive, or a diskette drive. Such types of memory storage devices typically read from, and/or write to, a program storage medium such as, respectively, a compact disk, magnetic tape, removable hard disk, USB or flash drive, or floppy diskette. Any of these program storage media, or others now in use or that may later be developed, may be considered a computer program product.

As will be appreciated, these program storage media typically store a computer software program and/or data. Computer software programs, also called computer control logic, typically are stored in system memory and/or the program storage device used in conjunction with memory storage device. In some embodiments, a computer program product is described comprising a computer usable medium having control logic (computer software program, including program code) stored therein. The control logic, when executed by a processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts. Input-output controllers could include any of a variety of known devices for accepting and processing information from a user, whether a human or a machine, whether local or remote. Such devices include, for example, modem cards, wireless cards, network interface cards, sound cards, or other types of controllers for any of a variety of known input devices.

Output controllers could include controllers for any of a variety of known display devices for presenting information to a user, whether a human or a machine, whether local or remote. In the presently described embodiment, the functional elements of a computer communicate with each other via a system bus. Some embodiments of a computer may communicate with some functional elements using network or other types of remote communications. As will be evident to those skilled in the relevant art, an instrument control and/or a data processing application, if implemented in software, may be loaded into and executed from system memory and/or a memory storage device.

All or portions of the instrument control and/or data processing applications may also reside in a read-only memory or similar device of the memory storage device, such devices not requiring that the instrument control and/or data processing applications first be loaded through input-output controllers. It will be understood by those skilled in the relevant art that the instrument control and/or data processing applications, or portions of it, may be loaded by a processor, in a known manner into system memory, or cache memory, or both, as advantageous for execution. Also, a computer may include one or more library files, experiment data files, and an internet client stored in system memory. For example, experiment data could include data related to one or more experiments or assays, such as detected signal values, or other values associated with one or more sequencing by synthesis (SBS) experiments or processes.

Additionally, an internet client may include an application enabled to access a remote service on another computer using a network and may for instance comprise what are generally referred to as "Web Browsers". In the present example, some commonly employed web browsers include Microsoft Internet Explorer available from Microsoft Corporation, Mozilla Firefox from the Mozilla Corporation, Safari from Apple Computer Corp., Google Chrome from the Google Corporation, or other type of web browser currently known in the art or to be developed in the future. Also, in the same or other embodiments an internet client may include, or could be an element of, specialized software applications enabled to access remote information via a network such as a data processing application for biological applications.

A network may include one or more of the many various types of networks well known to those of ordinary skill in the art. For example, a network may include a local or wide area network that may employ what is commonly referred to as a TCP/IP protocol suite to communicate. A network may include a network comprising a worldwide system of interconnected computer networks that is commonly referred to as the internet, or could also include various intranet architectures. Those of ordinary skill in the related arts will also appreciate that some users in networked environments may prefer to employ what are generally referred to as "firewalls" (also sometimes referred to as Packet, Filters, or Border Protection Devices) to control information traffic to and from hardware and/or software systems. For example, firewalls may comprise hardware or software elements or some combination thereof and are typically designed to enforce security policies put in place by users, such as for instance network administrators, etc.

Automated Systems for Staining

Exemplary automated systems available through Ventana Medical Systems, Inc., Tucson, Ariz. include SYMPHONY® Staining System, catalog #: 900-SYM3, VENTANA® BenchMark Automated Slide Preparation Systems, catalog #s: N750-BMKXT-FS, N750-BMKU-FS, VENTANA, and VENTANA® BenchMark Special Stains automated slide stainer. These systems employ a microprocessor controlled system including a revolving carousel supporting radially positioned slides. A stepper motor rotates the carousel placing each slide under one of a series of reagent dispensers positioned above the slides. Bar codes on the slides and reagent dispensers permits the computer controlled positioning of the dispensers and slides so that different reagent treatments can be performed for each of the various tissue samples by appropriate programming of the computer.

Illustrative instrumentation systems are designed to sequentially apply reagents to tissue sections mounted on one by three inch glass microscope slides under controlled environmental conditions. The instrument must perform several basic functions such as reagent application, washing (to remove a previously applied reagent), jet draining (a technique to reduce the residual buffer volume on a slide subsequent to washing), application of a light oil used to contain reagents and prevent evaporation, and other instrument functions. Exemplary staining instruments process slides on a rotating carousel. The slides maintain a stationary position and a dispenser carousel rotates the reagents above the fixed slides. The processes described herein can be performed using various physical configurations. The process of clarifying and staining tissue on a slide consists of the sequential repetition of basic instrument functions described above. Essentially a reagent is applied to the tissue then incubated for a specified time at a specific temperature. When the incubation time is completed the reagent is washed off the slide and the next reagent is applied, incubated, and washed off, etc., until all of the reagents have been applied and the staining process is complete.

For related disclosure, reference is made to Richards et al. U.S. Pat. No. 6,296,809, assigned to Ventana Medical Systems, which describes an apparatus and methods for automatically staining or treating multiple tissue samples mounted on microscope slides so that each sample can receive an individualized staining or treatment protocol even when such protocols require different temperature parameters. More specifically, what is described is an apparatus comprising a computer controlled, bar code driven, staining instrument that automatically applies chemical and biological reagents to tissue or cells mounted or affixed to standard glass microscope slides. A plurality of slides are mounted in a circular array on a carousel which rotates, as directed by the computer, to a dispensing location placing each slide under one of a series of reagent dispensers on a second rotating carousel positioned above the slides. Each slide receives the selected reagents (e.g. DNA probe) and is washed, mixed, and/or heated in an optimum sequence and for the required period of time.

Examples

The following examples are provided to illustrate certain specific features of working embodiments and general protocols. The scope of the present invention is not limited to those features exemplified by the following examples.

IHC Procedure

The following protocols were implemented on a VENTANA® BenchMark XT (VMSI Catalog #: N750-BMKXT-FS) with NexES V10.6, the ranges providing illustrative process variations with the bracketed values representing an exemplary value:

(1) Baking may be performed to adhere tissue to slides, especially for fresh cut slides; temperatures: 60° C.-75° C.; incubation time: 4-32 min; for online baking, set the temperature 2-4 degrees above the melting point of paraffin brand used, [No baking];

(2) Deparaffinization was performed to remove the wax for reagent penetration; the unique deparaffinization options include standard, extended and extended II; these procedures enable improved flexibility to allow greater success at optimizing difficult tissues; standard is the default and will reproduce the classic deparaffinization protocol using EZ Prep (VMSI Catalog #: 950-102); extended, when selected, will reproduce the deparaffinization from HER2 DDISH (VMSI Catalog #: 780-4422) (adding 5 extra EZ Prep rinsing steps to the standard protocol; extended II, when selected, will use LCS (VMSI Catalog #: 650-010), [Standard Deparaffinization, 75° C., 4 minutes; 3 EZ Prep rinses; 76° C., 4 minutes; Rinse];

(3) Pretreatment; on-slide post-fixation, option pretreatment, removal of excess protein (heat and enzyme); user-fillable fixative reagent; temperature from 37° C.-60° C.; user-fillable "FIXATIVE 1" through "FIXATIVE 10" incubation time from 4-32 min in Reaction Buffer; [No pretreatment];

(4) Cell Conditioning; used CC1 (VMSI Catalog #: 950-124), CC2 (VMSI Catalog #: 950-123) or Reaction Buffer (VMSI Catalog #: 950-300); CC1 with a slightly alkaline pH used for heat+buffer retrieval; CC2 pH of 6.0 used for heat+buffer retrieval, Reaction Buffer used for heat retrieval only; 1 to 5 cycles selectable; incubation times: 4-16 min; temperatures: 60° C.-100° C., [CC1 for 32 minutes-8 minutes at 95° C. followed by 24 minutes at 100° C.];

(5) Protease Treatment: cell conditioning using heat retrieval loosens crosslinks from fixation; protease "punches holes" in protein; combination may enable better sample penetration; enzyme choice and incubation time may be determined by reagent manufacturer, recommendation, experimentation, enzyme option; user-fillable dispensers to be used with ENZYME 1-10, pre-diluted Protease 1-3 (VMSI Catalog #s: 760-2018, 760-2019, 760-2020); pre-diluted ISH-Protease 1-3 (VMSI Catalog #s: 780-4147, 780-4148, 780-4149); incubation time from 4-32 min, [No protease used];

(6) Pre Primary Peroxidase Inhibit & Post Primary Peroxidase Inhibit (VMSI Catalog #: 253-4578); allows for inhibition of endogenous peroxidase after the primary has bound to the antigen; some antigens may be sensitive to hydrogen peroxide; this option can improve staining for those antibodies, [No Peroxidase Inhibition used];

(7) Apply rinsing reagent; Reaction Buffer; Apply LCS, [4 minutes, no heat];

(8) Clarification Process [described herein];

(9) Primary Antibody Application; primary antibody temperature and primary antibody dilution option; enables the user to modify the incubation temperature for the primary; adds an additional 900 µL of Reaction Buffer to the slide before primary antibody application; [anti-V600E (Clone VE1), Incubate 37° C. for 16 minutes];

(10) Detection links a "visual" molecule to the probe; UltraView or OptiView (VMSI Catalog #s: 760-500, 760-700) [OptiView]; and

(11) Counterstain & Post-counterstain; adds a "backdrop" color to the tissue; user can select from a list of counterstain reagents, including pre-dilute VENTANA reagents as well as user-fillable counterstain dispensers; incubation time is selectable from 4 min to 32 min; [counterstain 4 minutes with Hematoxylin II (VMSI Catalog #: 790-2208), Post-counterstain 4 minutes with Bluing Reagent (VMSI Catalog #: 760-2037)].

Breast Cancer Example

Cancerous breast tissue slides were stained with a cocktail of haptenated primary antibodies followed by sequential staining using anti-hapten secondary antibodies linked to HRP. The deposition of specific chromogens of different colors represented the localization of the primary antibodies. The stained slides were scanned and the corresponding RGB color images were obtained. To analyze the images, we developed a color unmixing algorithm to identify the individual constituent dyes for the biomarkers and the proportions in which they appear in the color images. Based on the separated image channels for each marker, detection algorithms were developed to automatically identify different types of T-cells. The image analysis was done for Oscar, CD3, CD8 and FP3 markers. As the final output, the score for each marker was reported.

We observed different combinations of the T-cell distributions in the slides and validated our analysis algorithm by identifying the number and location of each type of T-cell.

The multiplex assay, along with the image analysis algorithms, potentially provide a toolkit for the breast cancer immune score computation. The final report generated by the computer may be used to support the clinical analysis of the patient's personal immune response and help guide further breast cancer treatment, but further studies are needed to validate this approach.

For each case, manual cell counts and regional annotation were taken. The data for each patient were summarized as a median expression across sampled nodes, and these values were then compared between relapse and no relapse groups. There were statistically significant differences in the peri/intra ratio for both CD3 and CD8, with the ratio being higher in no relapse patients compared to relapse patients for both breast cohort.

Melanoma Example

We have collected FFPE lymphadenectomies from 34 melanoma patients, analyzing a total of 150 lymph-nodes. We have characterized the Immunoscore by immunohistochemistry expression of CD3, CD8, CD20 and Foxp3 (all Ventana Medical Systems). 3-4 µm serial tissue sections have been cut for haematoxylin/eosin (H&E) and stained with a multiplex of all markers including tumor marker for melanoma (S100). Tissue sections were stained using novel multiplex staining protocols on a VENTANA Benchmark instrument as well as serial section (slide) staining. Initial evaluation was conducted with a high power microscope field (Olympus BX51), excluding hemorrhagic or necrotic areas. The number of positive cells has been evaluated by counting them in 5 peritumoral and 5 intratumoral non-overlapping fields using ×400 magnification. The expression of each marker as well as combinations of markers have been matched with the most important clinical information that correlates with clinical outcome.

These trending differences also seemed apparent for both FoxP3 and CD20, although our limited sample size restricted some conclusions. We then hypothesized a high/low risk score which we now plan to validate on a larger melanoma. For each case, manual cell counts and regional annotation were taken. The data for each patient were summarized as a median expression across sampled nodes, and these values were then compared between relapse and no relapse groups. There were statistically significant differences in the peri/intra ratio for both CD3 and CD8, with the ratio being higher in no relapse patients compared to relapse patients for both proteins. These trending differences also seemed apparent for both FoxP3 and CD20, although our limited sample size limited some conclusions. We then hypothesized a high/low risk score which we now plan to validate on a larger cohort.

Image Analysis

A color unmixing algorithm, which may be refer referred to as a color unmixing algorithm, was developed that separates image data into individual contributions from three or more different chromogens. Tissue slides stained with the newly developed multiplex chromogen brightfield assay system were scanned on a standard brightfield whole-slide scanner and the color unmixing algorithm was applied in order to provide individual stain-specific image channels for subsequent analysis. As a model to apply this technology, we designed immune profiling assays for breast cancer tissue that consisted of antibodies targeting CD3+ T cells, CD8+ cytotoxic T cells, FoxP3+ Treg cells, CD20+B cells, CD68+ macrophages, and cytokeratin+ tumor cells.

We observed a range of immune responses, both in terms of different cell types and in terms of number of cells. In addition, immune cells were located in different regions of the tissue, such as: stroma only, at the invasive margin of the tumor, and in the tumor center. Various combinations of immune cell distribution were observed, and when correlated with clinical outcome these data may be predictive of patient responses.

SUMMARY

Detection and characterization of tumor-infiltrating lymphocytes (TILs) and macrophages in individual cancer patients serves to demonstrate to what extent the patient's own immune system is activated in response to the tumor. This information may then be used as a prognostic or predictive test, or as a guide to further therapy.

The multiplex chromogen detection system is a flexible and sensitive technology that can be used to detect multiple targets in brightfield light microscopy. For example, flexibility is demonstrated by the interchangeability of the chromogens and multiplexed assays can be designed using haptenated antibodies to improve sensitivity and avoid non-specific binding or "cross talk". By using hapten amplification, the signal generated is more robust and allows detection of weakly-expressed antigens.

The Immune Profiling concept illustrated in this filing serves as an ideal application for multiplex chromogen brightfield IHC, providing medical value by enabling multi-component tumor microenvironment analyses and facilitating testing efficiency by means of single slide staining.

The invention claimed is:

1. A computer-implemented method for counting a number of types of cells in a single tissue specimen that has been stained with a multiplex assay, comprising:
    imaging the single tissue specimen that has been stained with the multiplex assay that includes lymphocyte markers CD3, CD8, CD20, FoxP3, and tumor detection markers;
    unmixing the image of single tissue specimen that has been stained with a multiplex assay into separate image channels for each marker of the multiplex assay;
    identifying regions of interest in each image channel based on intensity information in each channel, wherein regions of low intensity in each channel are removed, and regions of high intensity represent cell signals;
    generating a single surrogated image, wherein the surrogated image is a combination of the image channel information of all the lymphocyte markers;
    applying a cell detection algorithm, wherein the cell detection algorithm is a membrane finding algorithm or a nucleus finding algorithm;
    identifying features of the lymphocytes and combinations of lymphocytes in each image channel or image of combined channels, or a transformed image such as grayscale or absorbance image, or a surrogated image;
    training a classification algorithm based on features of known lymphocytes and lymphocyte combinations;

applying the trained algorithm to features of the lymphocytes and combinations of lymphocytes in each image channel or image of combined channels, or a transformed image such as grayscale or absorbance image, or a surrogated image, that were identified to classify the detected cells as at least one of false positive cells, CD3 only T-cells, CD3 and CD8 T-cells, FP3 T-cells; and CD20 B-cells;

counting a number of each different type of cell classified;

generating a score the tissue specimen, wherein the score is based on the number each type of cell counted.

2. The method of claim 1, wherein said multiplex assay comprises:
contacting a sample with CD3, CD8, CD20, and FoxP3 specific binding moieties,
removing excess specific binding moieties from the sample, and
detecting the specific binding moieties.

3. The method of claim 2, wherein said multiplex assay further comprises contacting the sample with a specific binding moiety for a tumor marker.

4. The method of claim 3, wherein the specific binding moiety for the tumor marker is selected from antibodies to cytokeratin for epithelial tumors (carcinomas) and antibodies to S100 for melanomas.

5. The method of claim 2, wherein the specific binding moiety for CD3 is anti-CD3 rabbit or mouse monoclonal antibodies.

6. The method of claim 2, wherein the specific binding moiety for CD8 is anti-CD8 rabbit or mouse monoclonal antibodies.

7. The method of claim 2, wherein the specific binding moiety for CD20 is anti-CD20 rabbit or mouse monoclonal antibodies.

8. The method of claim 2, wherein the specific binding moiety for FoxP3 is anti-FoxP3 rabbit or mouse monoclonal antibodies.

9. The method of claim 2, wherein contacting comprises contacting the sample with CD3, CD8, CD20, and FoxP3 specific binding moieties which are selected from rabbit or mouse monoclonal antibodies.

10. The method of claim 9, wherein detecting comprises contacting the sample with an anti-species antibody specific to the rabbit or mouse monoclonal antibodies.

11. The method of claim 10, wherein the anti-species antibody is haptenated, and wherein detecting the haptenated antibody further comprises contacting the sample with an anti-hapten antibody conjugated to an enzyme.

12. The method of claim 11, wherein detecting further comprises contacting the sample with a detection compound.

13. The method of claim 12, wherein the detection compound is selected from a chromogen or a fluorophore.

14. The method of claim 2, wherein the specific binding moieties are haptenated, and wherein detecting the specific binding moieties further comprises contacting the sample with an anti-hapten antibody conjugated to an enzyme.

15. The method of claim 14, wherein detecting further comprises contacting the sample with a detection compound.

16. The method of claim 15, wherein the detection compound is selected from a chromogen or a fluorophore.

17. The method of claim 1, wherein the single tissue specimen is a tissue section.

* * * * *